United States Patent [19]

Backus et al.

[11] Patent Number: 5,559,013
[45] Date of Patent: Sep. 24, 1996

[54] METHOD OF AMPLIFICATION USING INTERMEDIATE RENATURATION STEP

[75] Inventors: John W. Backus, Williamson; John W. H. Sutherland, Rochester, both of N.Y.

[73] Assignee: Johnson & Johnson Clinical Diagnostics, Inc., Rochester, N.Y.

[21] Appl. No.: 264,102

[22] Filed: Jun. 22, 1994

[51] Int. Cl.$^6$ .............. C12P 19/34; C12Q 1/68; C12Q 1/70; C07H 21/04
[52] U.S. Cl. ............... 435/91.2; 435/6; 435/5; 536/24.3; 536/24.33
[58] Field of Search ............... 435/91.2, 6, 5; 536/24.3–24.33

[56] References Cited

U.S. PATENT DOCUMENTS

| | | | |
|---|---|---|---|
| 5,229,297 | 7/1993 | Schnipelsky et al. | 436/94 |
| 5,340,728 | 8/1994 | Grosz et al. | 435/91.2 |

OTHER PUBLICATIONS

Lehtovaara et al, Quantitative PCR for Hepatitis B Virus with Colorimetric detection. PCR Meth. and Applications 3:169–175, 1993.

Apostolakos et al, Measurement of Gene Expression by Multiplex Competitive PCR, Anal. Bioch. 213:277–284, 1993.

Pomp and Medrano, Organic Solvents as Facillitators of Polymerase Chain reaction, BioTechniques 10(1) 58–59, 1991.

Kellogg et al., *Anal. Biochem.*, 189, pp. 202–208 (1990).

Hurt et al., *Clin. Chem.*, 36 (6), p. 1019 (1990), Abstract 0314.

Gautelli et al., *Clin. Microbiol. Rev.*, 2 (2), pp. 217–226 (1989).

Pang et al., *Nature*, 343 (4), pp. 85–89 (1990).

*Primary Examiner*—W. Gary Jones
*Assistant Examiner*—Dianne Rees

[57] ABSTRACT

A method for amplification and detection of a low copy target nucleic acid includes coamplification of a high copy target nucleic acid. After a number of conventional amplification cycles which include a denaturation step, several cycles are carried out during which the denatured products are renatured for a brief period of time. This intermediate step in later cycles of the amplification process reduces the effective concentration of the high copy target nucleic acid available for amplification in later cycles, thereby making more DNA polymerase available for amplification of the low copy target nucleic acid.

15 Claims, No Drawings

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 28
        ( B ) TYPE: Nucleic Acid
        ( C ) STRANDEDNESS: Single
        ( D ) TOPOLOGY: Linear ( i i ) MOLECULE TYPE:Primer for HIV-I DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: US-A-5,147,777

( x i ) SEQUENCE DESCRIPTION: SEQ ID NO: 1:

ATAATCCACC TATCCCAGTA GGAGAAAT    2 8

( 2 ) INFORMATION FOR SEQ ID NO:2:

( i ) SEQUENCE CHARACTERISTICS:

( A ) LENGTH: 28
            ( B ) TYPE: Nucleic acid
            ( C ) STRANDEDNESS: Single
            ( D ) TOPOLOGY: Linear ( i i ) MOLECULE TYPE: Primer for HIV-I DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: US-A-5,147,777

( x i ) SEQUENCE DESCRIPTION: SEQ ID NO: 2:

TTTGGTCCTT GTCTTATGTC CAGAATGC                                                        2 8

( 2 ) INFORMATION FOR SEQ ID NO:3:

( i ) SEQUENCE CHARACTERISTICS:
            ( A ) LENGTH: 20
            ( B ) TYPE: Nucleic acid
            ( C ) STRANDEDNESS: Single
            ( D ) TOPOLOGY: Linear ( i i ) MOLECULE TYPE: Primer for b-globin DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: US-A-5,147,777

( x i ) SEQUENCE DESCRIPTION: SEQ ID NO: 3:

CAACTTCATC CACGTTCACC                                                                 2 0

( 2 ) INFORMATION FOR SEQ ID NO:4:

( i ) SEQUENCE CHARACTERISTICS:
            ( A ) LENGTH: 20
            ( B ) TYPE: Nucleic acid
            ( C ) STRANDEDNESS: Single
            ( D ) TOPOLOGY: Linear ( i i ) MOLECULE TYPE: Primer for b-globin DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: US-A-5,147,777

( x i ) SEQUENCE DESCRIPTION: SEQ ID NO: 4:

ACACAACTGT GTTCACTAGC                                                                 2 0

( 2 ) INFORMATION FOR SEQ ID NO:5:

( i ) SEQUENCE CHARACTERISTICS:
            ( A ) LENGTH: 41
            ( B ) TYPE: Nucleic acid
            ( C ) STRANDEDNESS: Single
            ( D ) TOPOLOGY: Linear (i i) MOLECULE TYPE: Probe for HIV-I DNA (i i i) HYPOTHETICAL: No (i v) ANTI-SENSE: No (v i) ORIGINAL SOURCE: Synthetically prepared (v i i) IMMEDIATE SOURCE: Same (x) PUBLICATION INFORMATION: US-A-5,147,777

(x i) SEQUENCE DESCRIPTION: SEQ ID NO: 5:

ATCCTGGGAT TAAATAAAAT AGTAAGAATG TATAGCCCTA C  41

(2) INFORMATION FOR SEQ ID NO:6:

(i) SEQUENCE CHARACTERISTICS:
(A) LENGTH: 31
(B) TYPE: Nucleic acid
(C) STRANDEDNESS: Single
(D) TOPOLOGY: Linear (i i) MOLECULE TYPE: Probe for b-globin DNA (i i i) HYPOTHETICAL: No (i v) ANTI-SENSE: No (v i) ORIGINAL SOURCE: Synthetically prepared (v i i) IMMEDIATE SOURCE: Same (x) PUBLICATION INFORMATION: US-A-5,147,777

(x i) SEQUENCE DESCRIPTION: SEQ ID NO: 6:

CCTCAAACAG ACACCATGGT GCACCTGACT C  31

METHOD OF AMPLIFICATION USING INTERMEDIATE RENATURATION STEP

FIELD OF THE INVENTION

This invention relates to a rapid preferential coamplification of two or more double-stranded nucleic acids whereby a renaturation step is included among multiple amplification cycles.

BACKGROUND OF THE INVENTION

Detection of nucleic acids has grown in recent years as a means for early detection of genomic features, infectious agents and various organisms which are present in very small quantities in a human or animal test specimen. Detection procedures are normally based on the concept of complementarity whereby two DNA strands are bound together by hydrogen bonds and other forces between complementary nucleotides (which are known as nucleotide pairs).

A DNA molecule is normally quite stable, but the strands can be separated or denatured by certain conditions, such as heating. The denatured strands will reassociate only with another strand having a complementary sequence of nucleotides.

Much research has been carried out to find ways to detect only a few molecules of a DNA. Various procedures are known and have been used for almost a decade to amplify or greatly multiple the number of nucleic acids in a specimen for detection. Such amplification techniques include polymerase chain reaction (PCR), ligase chain reaction (LCR) and others which are less developed.

PCR is the most well known and involves the hybridization of primers to the strands of a target nucleic acid in the presence of a DNA polymerization agent and deoxyribonucleotide triphosphates under appropriate conditions. The result is the formation of primer extension products throughout several cycles and exponential multiplication of the number of original target strands. Further details about PCR can be obtained by consulting U.S. Pat. No. 4,683,195 (Mullis et al), U.S. Pat. No. 4,683,202 (Mullis) and U.S. Pat. No. 4,965,188 (Mullis et al).

Human and animal specimens contain many different nucleic acids, some of which are endogenous (or natural) to the person or animal, and others which are produced because of some abnormal condition, such as from the presence of an infectious agent or an oncogenic condition. Such nucleic acids are usually present in very low concentrations compared to endogenous nucleic acids. They are sometimes referred to as "low copy number" nucleic acids. By comparison, the endogenous nucleic acids are usually present in high concentrations and may be referred to as "high copy number" nucleic acids. One such example is human β-globin DNA.

Frequently, in using PCR, two or more nucleic acids present in the specimen are amplified at the same time in the same reaction container. This is identified herein as "coamplification". This process requires that primers for each nucleic acid to be amplified must be simultaneously present in the container.

When both low and high copy target nucleic acids are amplified in such situations, amplification of the low copy target nucleic acid is often inhibited. This is due to the saturation of the amplifying enzyme (such as DNA polymerase) by the high copy target nucleic acid during the later cycles of amplification. False negative results for the presence of the low copy target nucleic acid would be likely, with possibly serious consequences.

Various solutions to the problem have been proposed for PCR, including adjusting the concentrations of the primers, utilizing primer sets with specific melting temperatures (Tm's), or combinations thereof. Adjusting the primer ratios has been referred in the art as "primer biasing" the PCR yield, and requires a decrease in the concentration of primers for the high copy target nucleic acid. Only modest control of the process is achieved with this approach.

Another approach to coamplification has been to adjust the temperature of annealing in PCR such that the primers for the high copy target nucleic acid anneal to a lesser extent than those for the low copy target nucleic acid. This approach also has a problem. The $T_m$ difference between primer pairs must be relatively large before good modulation of PCR can be exerted on the differential yields for the high and low copy nucleic acids. Exact $T_m$'s cannot be calculated (although they can be estimated), and thus they must be measured. This requires a high degree of effort, and considerable tedium.

All of these approaches to modulate coamplification require that the high and low copy target nucleic acid sequences be known.

Alternatively, adding time to the priming or extension steps in PCR in later cycles can minimize the DNA polymerase saturation by the high copy target nucleic acid and increase amplification efficiency. However, this solution has limited utility in situations where many nucleic acids which are present in varying concentrations, are being amplified simultaneously.

It would be desirable to achieve rapid and efficient amplification of one or more low copy target nucleic acids when coamplified in the presence of one or more high copy target nucleic acids.

SUMMARY OF THE INVENTION

The problems noted above have been overcome with a method for the coamplification of two or more target nucleic acids, the method comprising:

I) at least 15 primary amplification cycles of from about 20 to about 360 seconds each, each cycle comprising the sequential steps of:
  A) heating a reaction mixture of two or more target nucleic acids or their primer extension products, at least one of the target nucleic acids being a low copy target nucleic acid, and at least one other of the target nucleic acids being a high copy target nucleic acid which is suspected of being present at at least about 1000 times the concentration of the low copy nucleic acid, the heating being carried out at a first temperature, $T_1$, of from about 85° to about 100° C. for denaturation of the strands of the high and low copy target nucleic acids or their primer extension products, B) priming the denatured strands with a set of primers specific to and hybridizable with opposing strands of each target nucleic acid to be amplified, by cooling to a second temperature, $T_2$, which is defined as:

$$(T_{mH}-15)°C. \leq T_2 \leq (T_{mH}+5)°C.$$

wherein $T_{mH}$ is the melting temperature of the primers for the high copy target nucleic acid, C) either as a continuation of step B) or in a different step, forming primer extension products in a reaction mixture of PCR reagents, by incubation at a third temperature, $T_3$, which is defined as:

$$(T_{mH}-15)°C. \leq T_3 \leq (T_{mH}+15)°C.,$$

provided that when priming and primer extension products formation are carried out in the same step, $T_2$ and $T_3$ are the same, and II) at least 5 secondary amplification cycles of from about 20 to about 360 seconds each, each cycle comprising repeating steps A) through C) identified above sequentially, provided that between steps A) and B) of each secondary amplification cycle, the reaction mixture is cooled to and maintained at a fourth temperature, $T_4$, which is defined as:

$$(T_{mH}+5)°C. \leq T_4 \leq T_{pH}$$

wherein $T_{pH}$ is the melting temperature of the double strands of the high copy target nucleic acid, for from about 15 to about 120 seconds.

The present invention provides a very rapid and efficient method for preferentially amplifying and detecting a low copy target nucleic acid, especially in the presence of high copy target nucleic acids which potentially obscure the signal for the low copy target nucleic acid. Thus, inhibition of the low copy target nucleic acid amplification by the high copy target nucleic acid, is reduced.

These advantages are achieved by including a renaturation step within the later cycles of the amplification process so that after a certain number of amplification cycles (identified herein as "primary" cycles), the amplified products are renatured or hybridized for a brief period of time after each denaturation step in subsequent cycles (identified herein as "secondary" cycles). The renaturation step is carried out at a temperature at which the complementary strands of the denatured products can readily renature or hybridize. However, the temperature is maintained above that at which the high copy target nucleic acid primers efficiently anneal to the complementary strands of the denatured amplified product. A sufficient amount of time is allowed for renaturation, thereby reducing the effective concentration of high copy target nucleic acid available for priming and subsequent amplification. This allows more efficient amplification of the low copy target nucleic acid in subsequent cycles as more DNA polymerase is available.

DETAILED DESCRIPTION OF THE INVENTION

The general principles and conditions for amplification and detection of nucleic acids using polymerase chain reaction are quite well known, the details of which are provided in numerous references including U.S. Pat. No. 4,683,195, U.S. Pat. No. 4,683,202 and U.S. Pat. No. 4,965,188 (noted above), all of which are incorporated herein by reference. Thus, in view of the teaching in the art and the specific teaching provided herein, a worker skilled in the art should have no difficulty in practicing the present invention by making the adjustments taught herein to coamplify two or more nucleic acids, one of which is a low copy target nucleic acid.

Other amplification procedures which can be used in the practice of this invention include ligase chain reaction as described, for example, in EP-A-0 320 308 (published December, 1987) and EP-A-0 439 182 (published January, 1990), and any other known amplification procedure which includes a product denaturation step. Thus, the teaching provided herein would allow one skilled in the art to adapt the renaturation modification shown for PCR to these other known amplification procedures. The remainder of this disclosure is directed to practicing the invention using PCR for illustrative purposes.

The present invention is directed to the amplification and detection of one or more specific nucleic acid sequences present in one or more low copy target nucleic acids in a test specimen simultaneously with the amplification of one or more nucleic acid sequences present in one or more high copy target nucleic acids. Generally, a low copy target nucleic acid is present in a specimen in an amount of less than about $10^{-16}$ molar, however, the amount can be greater if the high copy nucleic acids are present in much higher amounts, for example, at least 1000 times greater in concentration. High copy target nucleic acids are those generally associated with single copy genes while low copy target nucleic acids are generally those associated with infectious agents, cancers and other pathological conditions in a human or animal.

In addition, the high copy target nucleic acid can be used as a "positive control" in an assay. By modulating the efficiency of PCR of the high copy target nucleic acid, the positive control can be detectable only if PCR was carried out efficiently, thereby reducing the probability of false negatives. In such instances, the high copy target nucleic acid may be present at 10 or more times the concentration of the low copy target nucleic acid.

Test specimens can include cellular or viral material, hair, body fluids or other materials containing genetic DNA or RNA which can be detected. Target nucleic acids can be obtained from various sources including plasmids, and naturally occurring DNA or RNA from any source (such as bacteria, yeast, viruses, plants, higher animals or humans). It may be extracted from various tissues including blood, peripheral blood mononuclear cells (PBMC), other tissue materials or other sources known in the art using known procedures. The present invention is particularly useful for the coamplification and detection of nucleic acid sequences found in genomic DNA, bacterial DNA, fungal DNA, viral RNA, or DNA or RNA found in bacterial or viral infected cells. In addition, nucleic acid sequences associated with cancer markers are amplifiable and detectable using the present invention.

Bacteria which can be detected include, but are not limited to, bacteria found in human blood, Salmonella species, Chlamydia species, Gonococcal species, Shigella species and Mycobacterium species. Viruses which are detectable include, but are not limited to, herpes simplex viruses, Epstein Barr virus, human cytomegalovirus, human papilloma virus, hepatitis viruses and retroviruses such as HTLV-I, HTLV-II, HIV-I and HIV-II. Protozoan parasites, yeasts and molds are also detectable. Other detectable species would be readily apparent to one skilled in the art. The invention is particularly useful for the detection of the presence of DNA associated with a retroviral DNA (HIV-I or HIV-II) or a Mycobacterium species. Most preferably, it is used to detect DNA associated with HIV-I.

A "PCR reagent" refers to any of the reagents considered essential to PCR, namely a set of primers for the opposing strands of each target nucleic acid, a DNA polymerase, a DNA polymerase cofactor, and two or more deoxyribonucleoside-5'-triphosphates (dNTP's).

The term "primer" refers to an oligonucleotide, whether naturally occurring or synthetically produced, which is capable of acting as a point of initiation of synthesis when placed under conditions in which synthesis of a primer extension product complementary to a nucleic acid strand (that is, template) is induced. Such conditions include the presence of the other PCR reagents, and suitable temperature and pH. The primer must be long enough to prime the synthesis of extension products in the presence of the DNA polymerase. The exact size of each primer will vary depending upon the use contemplated, the complexity of the targeted sequence, reaction temperature and the source of the primer. Generally, the primers used in this invention will have from 10 to 60 nucleotides.

Primers can be obtained from a number of sources or prepared using known techniques and equipment, including for example, an ABI DNA Synthesizer (available from Applied Biosystems) or a Biosearch 8600 Series or 8800 Series Synthesizer (available from Milligen-Biosearch, Inc.) and known methods for their use (for example as described in U.S. Pat. No. 4,965,188, noted above). Naturally occurring primers isolated from biological sources are also useful (such as restriction endonuclease digests). A set of at least two primers is generally used for each target nucleic acid. Thus, a plurality of sets of primers can be used simultaneously to amplify a plurality of target nucleic acids. In addition, a set of primers can include a mixture of primers for a given target nucleic acid.

DNA polymerases are well known as enzymes which will esterify and add deoxynucleoside monophosphate molecules to the 3'-hydroxy end of the primer by a phosphodiester linkage to the primer, with synthesis being template directed. Useful DNA polymerases include for example, *E. coli* DNA polymerase I, T4 DNA polymerase, Klenow polymerase, reverse transcriptase and others known in the art.

The DNA polymerase is preferably "thermostable", meaning that it is generally stable at the high temperatures used for denaturation of DNA strands. More particularly, the thermostable DNA polymerases are not substantially inactivated at the high temperatures used in PCR. Such temperatures will vary depending upon a number of reaction conditions, including pH, salt concentration, and other conditions known in the art.

A number of thermostable DNA polymerases have been reported in the art, including those mentioned in detail in U.S. Pat. No. 4,965,188 (noted above) and U.S. Pat. No. 4,889,818 (Gelfand et al), incorporated herein by reference. Particularly useful polymerases are those obtained from various Thermus bacterial species, such as *Thermus aquaticus, Thermus filiformis, Thermus flavus* or *Thermus thermophilus*. Other useful thermostable polymerases are obtained from a variety of other microbial sources including *Thermococcus literalis, Pyrococcus furiosus*, Thermotoga sp. and those described in WO-A-89/06691 (published Jul. 27, 1989). Some useful enzymes are commercially available. A number of techniques are known for isolating naturally-occurring polymerases from organisms. Cloning and other synthetic techniques for preparing polymerases using recombinant techniques are also known from the art cited above, including the Gelfand et al patent.

A DNA polymerase cofactor refers to a nonprotein compound on which the enzyme depends for activity. A number of such materials are known in the art, including manganese and magnesium salts. Useful cofactors include, but are not limited to, manganese and magnesium chlorides, sulfates, acetates and fatty acid salts. The chlorides, sulfates and acetates are preferred, and the magnesium chlorides and sulfates are most preferred.

Also needed for PCR are two or more deoxyribonucleoside-5'-triphosphates, such as dATP, dCTP, dGTP, dTTP and dUTP. Analogues such as dITP and 7-deaza-dGTP are also useful. Preferably, the four common triphosphates (dATP, dCTP, dGTP and dTTP) are used in PCR.

Also useful in the practice of the invention is an antibody specific to the DNA polymerase, which antibody inhibits its enzymatic activity at temperatures below about 50° C., but which antibody is deactivated at higher temperatures. Representative monoclonal antibodies having these properties are described in recently allowed U.S. Ser. No. 07/958,144 (filed Oct. 7, 1992 by Scalice et al), incorporated herein by reference. Antibody fragments can be used in place of the whole molecule.

The PCR reagents described herein are provided and used in PCR in suitable concentrations to provide amplification of the target nucleic acid. The minimal amounts of DNA polymerase is generally at least about 1 unit/100 μl of solution, with from about 4 to about 25 units/100 μl being preferred. A "unit" is defined herein as the amount of enzyme activity required to incorporate 10 nmoles of total nucleotides (dNTP's) into an extending nucleic acid chain in 30 minutes at 74° C. The concentration of each primer is at least about 0.075 μmolar with from about 0.1 to about 2 μmolar being preferred. The primers can be present in the same or different amounts. Preferably, the primers of each set of primers for each target nucleic acid are initially present in the reaction mixture in the same amount. The cofactor is generally present in an amount of from about 1 to about 15 mmolar, and each dNTP is generally present at from about 0.15 to about 3.5 mmolar in the reaction mixture.

The PCR reagents can be supplied individually, or in a buffered solution having a pH in the range of from about 7 to about 9 using any suitable buffer. Thus, a reaction mixture for PCR can contain a set of primers for a low copy target nucleic acid, a set of primers for a high copy target nucleic acid, suitable dNTP's, a thermostable DNA polymerase, a cofactor for the DNA polymerase, and any other addenda that one skilled in the art would consider useful in the amplification or eventual detection of the target nucleic acids.

A target nucleic acid can be obtained from any of a variety of sources as noted above. Generally, it must be extracted in some manner to make it available for contact with the primers and other reaction materials. This usually means removing unwanted proteins and cellular matter from the specimen in a suitable manner. Various procedures are known in the art, including those described by Laure et al in *The Lancet*, pp. 538–540 (Sep. 3, 1988), Maniatis et al, *Molecular Cloning: A Laboratory Manual*, pp. 280–281 (1982), Gross-Belland et al in *Eur. J. Biochem.*, 36, 32 (1973) and U.S. Pat. No. 4,965,188 (noted above). Extraction of DNA from whole blood or components thereof are described, for example, in EP-A-0 393 744 (published Oct. 24, 1990), Bell et al, *Proc. Natl. Acad. Sci. USA*, 78(9), pp. 5759–5763 (1981), Saiki et al, *Bio/Technology*, 3, pp. 1008–1012 (1985) and U.S. Pat. No. 5,231,015 (Cummins et al). The particular extraction procedure is not essential to the practice of the present invention.

Since the target nucleic acid to be amplified and detected is usually in double strand form, the two strands must be separated (that is, denatured) before priming can take place. This can occur during the extraction process, but preferably, it occurs in a separate step afterwards. Heating to a suitable temperature (identified as "first temperature" or $T_1$ herein) is a preferred means for denaturation. Generally, this first temperature is in the range of from about 85° to about 100° C. for a suitable time, for example from 1 to about 240 seconds (preferably 1 to about 40 seconds). This initial denaturation step can also be included in the first amplification cycle. In such instances, denaturation may be longer in the first cycle (for example, up to 240 seconds) whereas later cycles can have much shorter denaturation steps (for example, up to 30 seconds).

The denatured strands are then primed with the appropriate set of primers by cooling the reaction mixture to a second temperature, $T_2$, which is generally within the range of from about 55° to about 70° C. It is desired that cooling is done quickly as possible, but with presently known equipment, it generally takes place over a time period of from about 5 to about 40 seconds, and more preferably for from about 5 to about 20 seconds. Preferably, $T_2$ is defined as:

$$(T_{mH}-15)°C. \leq T_2 \leq (T_{mH}+5)°C.$$

wherein $T_{mH}$ is the melting temperature of the primers for the high copy target nucleic acid.

Once the denatured strands are cooled, the reaction mixture containing the PCR reagents is incubated at a third temperature, $T_3$, generally for from 1 to about 120 seconds, and preferably for from 1 to about 80 seconds, to effect formation of primer extension products. Generally, the third temperature is defined as:

$$(T_{mH}-15)°C. \leq T_3 \leq (T_{mH}+15)°C.$$

and is generally within the range of from about 55° to about 70 ° C. Preferably, it is within the range of from about 62° to about 68° C.

In a most preferred embodiment, the second and third temperatures are the same and are within the range of from about 62° to about 68° C. Thus, priming and primer extension are preferably carried out in the same step.

Each primer for the high copy target nucleic acid also has a melting temperature identified herein as $T_{mH}$. Usually, the difference between $T_{mL}$ and $T_{mH}$ is from 0° to about 8° C., and both $T_2$ and $T_3$ are usually lower than $T_{mL}$ or $T_{mH}$ or equal to either $T_{mL}$ or $T_{mH}$.

Melting temperature is defined herein as the temperature at which one-half of a primer is denatured from a complementary strand (such as the template). The determination of the melting temperatures can be accomplished using several standard procedures, based on ultraviolet hypochromism, for example, by monitoring the spectrum at 260 nm as described in *Biochemistry-The Molecular Basis Of Cell Structure and Function*, 2d Edition, Lehninger, Worth Publishers, Inc., 1970, pp. 876–7. The various methods of determining melting temperatures may produce slightly differing values for the same DNA molecule, but those values should not vary by more than about 2° or 3° C. Moreover, the difference between $T_{mL}$ and $T_{mH}$ should not vary within a given method for determining melting temperatures.

Preferably, the melting temperatures are calculated using the formula:

$$T_m(° C.)=67.5+0.34(\% G+C)-395/N$$

wherein "G" and "C" represent the number of guanine and cytosine nucleotides, respectively, and "N" represents the total number of nucleotides in the oligonucleotide (that is, the primer). Melting temperature values obtained by this calculation correlate very well with the values determined empirically at room temperature using conventional UV hypochromism and a conventional Hewlett-Packard diode array spectrophotometer (scanning rate of about +1° C./min.) for a solution of primer in 10 mmolar tris(hydroxymethyl)aminomethane buffer (pH 8.5) having an ionic strength of at least about 20 mmolar provided by one or more inorganic or organic salts, such as magnesium chloride, sodium chloride and others readily apparent to one skilled in the art. The amounts of primer and its complement in the solution used to determine the noted melting temperature formula were sufficient to provide an optical density of from about 0.5 to about 1.0 OD units.

Thus, a "primary" amplification cycle comprises the denaturation, priming (or annealing) and primer extension steps described above. Generally, at least 15 of such primary amplification cycles are carried out in the practice of this invention with the maximum number of cycles being within the discretion of the particular user. In most instances, 15 to 35 primary amplification cycles are used in the method with 25 cycles being preferred. Each primary amplification cycle is generally from about 20 to about 360 seconds, with a cycle time of from about 30 to about 120 seconds being preferred and from about 30 to about 90 seconds being more preferred. However, longer or shorter cycle times can be used if desired.

After at least 15 primary amplification cycles as defined above, subsequent or "secondary" amplification cycles are carried out having the same steps, except that a renaturation step is included after each denaturation step and before the priming step.

Renaturation is accomplished by cooling the reaction mixture to a fourth temperature, $T_4$, defined as:

$$(T_{mH}+5)°C. \leq T_4 \leq T_{pH}$$

wherein $T_{pH}$ is the melting temperature of the double strands of the high copy target nucleic acid being detected. Generally, $T_4$ is from about 65° to about 90° C. The time needed to reach $T_4$ is as short as possible, but it may be up to about 45 seconds, and that temperature can be maintained for from about 15 to about 100 seconds.

At least 5 secondary amplification cycles are used in the method with an upper limit being at the discretion of the user. Preferably, the method includes from 5 to 20 secondary cycles, and 15 cycles are most preferred. The time for each secondary cycle is from about 20 to about 360 seconds. A preferred cycle time is from about 30 to about 120 seconds.

As used in this application, when used in reference to time for a given step, the term "about" refers to ±10% of that time limit. When used in reference to temperatures, the term "about" refers to ±5° C.

The kinetics of nucleic acid hybridization reactions, such as renaturation of amplification products, are linearly related to the concentration of the nucleic acids being hybridized. Therefore, as the concentration of amplified product increases for example, 10 times, the hybridization rate also increases 10 times (and the $t_{1/2}$ for renaturation decreases 10 times). Assuming a forward rate constant for hybridization of $5\times10^6$ molar$^{-1}$ sec$^{-1}$, the $t_{1/2}$ would be about 14 seconds at a product concentration of $10^{-8}$ molar, and 140 seconds at a product concentration $10^{-9}$ molar.

Inclusion of a product renaturation step in the later cycles at a temperature at or below the effective high copy product $T_m$ (melting temperature) but several degrees above the effective $T_m$ of the primers used in the amplification reaction allows for renaturation of amplification products in a concentration dependent manner. The relatively short renaturation step of the secondary cycles does not substantially affect the efficiency of priming of the low copy target nucleic acid, but will decrease priming of the high copy target nucleic acid.

The amplification method of this invention is preferably conducted in a continuous, automated manner so that the reaction mixture is temperature cycled in a controlled manner for a desired number of times. A number of instruments have been developed for this purpose, as one of ordinary skill in the art would know. Preferably, the instrument used will also be programmable for the renaturation step and the resumption of amplification cycles thereafter.

One such instrument for this purpose is described in some detail in U.S. Pat. No. 4,965,188 and EP-A-0 236,069. Generally, this instrument includes a heat conducting container for holding a number of reaction tubes containing reaction mixture, a means for heating, cooling and temperature maintenance, and a computing means to generate signals to control the amplification sequence, changes in temperature and timing.

EP-A-0 402 994 provides details of useful chemical test packs which can be processed using the instrument described in U.S. Pat. No. 5,089,233 (Devaney, Jr. et al), incorporated herein by reference. Also described therein are means for heating and cooling the test pack at repeated intervals (that is, through cycles) appropriate for the method of the present invention. Further details regarding useful PCR processing equipment can be obtained from the considerable literature in the field, and would be readily known by one skilled in the art.

Besides chemical test packs described above, the method can be carried out in other containers such as those described in more detail in U.S. Pat. No. 4,902,624 (Columbus et al), U.S. Pat. No. 5,173,260 (Zander et al) and U.S. Pat. No. 5,229,297 (Schnipelsky et al), all incorporated herein by reference, and any other suitable container which is readily apparent to one skilled in the art.

Detection of amplified products can be accomplished using any known procedure, including Southern blotting techniques, as described in U.S. Pat. No. 4,965,188 (noted above), or by use of labeled probes or primers, as is known in the art.

Alternatively to the embodiments described above, the amplified products can be detected using a labeled oligonucleotide which is complementary to one of the primer extension products. Procedures for attaching labels to oligonucleotides are well known. Useful labels include enzymes, ferritin and other magnetic particles, radioisotopes, chemiluminescent reagents (for example, luminol), biotin and various fluorogens and chromogens. Useful enzyme labels include glucose oxidase, peroxidase and alkaline phosphatase. Substrates and dye providing reagents for various labels, such as enzymes, are also known.

In a preferred embodiment, an enzyme label (such as peroxidase) is used for detection, and a suitable composition for providing a dye or light emission is used with that label. For example, particularly useful colorimetric dye providing systems are described in U.S. Pat. No. 5,024,935 (McClune et al). Detection is then achieved either using the unaided eye, or with suitable spectrophotometers or luminometers.

It is also possible that one of the primers of each primer set used in the method is labeled with a specific binding moiety. This moiety can be the same or different for various primers, and include any molecule for which there is a specific binding receptor which reacts specifically with that moiety. Examples of specific binding pairs (one of which can be the label) include, but are not limited to, streptavidin/biotin, sugar/lectin, antibody/hapten, antibody/antigen and other readily apparent to one skilled in the art. The receptor molecule is then conjugated with a suitable detectable label moiety such as an enzyme, radioisotope or others described above for oligonucleotides.

More preferably, one or both primers of each primer set are labeled with biotin (or an equivalent derivative thereof), and the amplified product is detected using a conjugate of streptavidin and an enzyme, such as horseradish peroxidase.

In heterogeneous detection systems of this invention, the amplified products are captured on a water-insoluble substrate of some kind, and the other materials in the reaction mixture are removed in a suitable manner, such as by filtration, centrifugation, washing or another separation technique.

Capture probes can be attached to water-insoluble supports using known attachment techniques (including absorption and covalent reactions). One such technique is described in EP-A-0 439 222 (published Sep. 18, 1991). Other techniques are described, for example, in U.S. Pat. No. 4,713,326 (Dattagupta et al), U.S. Pat. No. 4,914,210 (Levenson et al) and EP-B-0 070 687 (published Jan. 26, 1983). Useful separation means include filtration through membranes such as polyamide microporous membranes commercially available from Pall Corporation.

However, any useful solid support can be used to anchor the capture probe and eventual hybridization product, including microtiter plates, test tubes, beakers, magnetic or polymeric particles, metals, ceramics, and glass wool to name a few. Particularly useful materials are magnetic or polymeric particles having reactive groups useful for covalently attaching the capture probe. Such particles are generally from about 0.001 to about 10 μmeters. Further details about examples of such materials are provided in U.S. Pat. No. 4,997,772 (Sutton et al), U.S. Pat. No. 5,147,777 (Sutton et al), U.S. Pat. No. 5,155,166 (Danielson et al) and U.S. Pat. No. 4,795,698 (Owen et al), all incorporated herein by reference.

The capture probe can be affixed to a flat support such as a polymeric film, membranes, filter papers, or resin-coated or uncoated paper. Capture probe affixed to polymeric particles can also be immobilized on such flat supports in a suitable manner, for example, as dried deposits, or adhered by heat fusion or with adhesives. Other details of such materials are provided in EP-A-0 408 738 (published Jan. 23, 1991), WO 92/16659 (published Oct. 1, 1992) and U.S. Pat. No. 5,173,260 (Sutton et al).

The capture probes can be arranged on a suitable support in any configuration, for example rows of round deposits or stripes.

The following examples are included to illustrate the practice of this invention, and are not meant to be limiting in any way. All percentages are by weight unless otherwise noted.

Materials and Methods for Examples

The primers used in the Examples had the following sequences. The first two are complementary to the gag region of HIV-I DNA, and the second two primers are complementary to β-globin DNA.

SEQ ID NO:1: 5'-X-ATAATCCACC TATCCCAGTA GGAGAAAT-3'

SEQ ID NO:2: 5'-X-TTTGGTCCTT GTCTTATGTC CAGAATGC-3'

SEQ ID NO:3: 5'-X-CAACTTCATC CACGTTCACC-3'

SEQ ID NO:4: 5'-ACACAACTGT GTTCACTAGC-3'.

In the primers, X represents a biotinyl moiety (derived from a biotin phosphoramidite reagent, DuPont) appended to the oligonucleotide through two aminotetraethylene glycol spacer groups using the technology described in U.S. Pat. No. 4,962,029 (Levenson et al).

The capture probes used in the Examples had the following sequences, the first being for HIV-I and the second for β-globin DNA:

SEQ ID NO:5: 5'-ATCCTGGGAT TAAATAAAAT AGTAAGAATG TATAGCCCTA C-Y-3'

SEQ ID NO:6: 5'-CCTCAAACAG ACACCATGGT GCACCTGACT C-Y-3'

"Y" represents two tetraethylene glycol spacers connected to a single aminediol linking group using the teaching of U.S. Pat. No. 4,914,210 (Levenson et al).

The primers and capture probes were prepared using known starting materials and procedures using an Applied Biosystems Model 380B, three column DNA synthesizer, standard phosphoramidite chemistry and the ABI 1 μmolar scale, fast cycle protocol. Nucleoside-3'-phosphoramidites and nucleoside derivatized controlled pore glass supports were obtained from Applied Biosystems. All purifications were carried out using a nucleic acid purification column, followed by reversed phase HPLC techniques.

To form capture reagents, the probes were covalently attached to polymeric particles (1 μm average diameter) prepared, using conventional emulsion polymerization techniques, from poly[styrene-co-3-(p-vinylbenzylthio)propionic acid] (95:5 weight ratio, 1 μm average diameter). A suspension of the particles in water was washed with 2-(N-morpholino)ethanesulfonic acid buffer (0.1 molar, pH 6), and suspended to about 10% solids. A sample (3.3 ml) of the washed particles, diluted to 3.33% solids in the buffer (0.1 molar, was mixed with 1-(3-dimethylaminopropyl)-3-ethylcarbodiimide hydrochloride (2.1 ml of 84 mg/ml water) and the probe (983 μl of 44.44 OD/ml nanopure water). The resulting suspension was heated at 50° C. in a water bath for about two hours with intermittent mixing and centrifuged. The particles were then washed three times with tris(hydroxymethyl)aminomethane buffer (0.01 molar, pH 8) containing (ethylenedinitrilo)tetraacetic acid disodium salt (0.0001 molar) and resuspended therein to 4% solids.

Upon dilution to 0.25% solids with buffer, the capture reagents (1.2 μl) were applied to and dried in defined regions of the microporous membranes (LOPRODYNE™ polyamide membrane, 5 μm average pore size, from Pall Corp.) in the test wells of SURECELL™ disposable test devices (available from Eastman Kodak Company), which are described in detail in U.S. Pat. No. 4,948,561 (Hinckley et al).

PCR was carried out using an automated Kodak PCR processor which is described in detail in U.S. Pat. No. 5,089,233, incorporated herein by reference, using the heating and cooling protocol described in the Examples below.

Recombinant DNA polymerase from *Thermus aquaticus* was obtained using conventional procedures.

Glycerol, tris(hydroxymethyl)aminomethane buffer and the dNTP's were obtained from Sigma Chemical.

Low copy target HIV-I DNA was extracted from the 8E5/LAV cell line using conventional procedures. Following cell lysis and protein digestion, the DNA was purified by phenol/chloroform extraction: tris-saturated phenol (750 μl) was added to the cell suspension, and phenol/lysate solutions were mixed and separated by centrifugation. The aqueous phase was then transferred into a fresh 2 ml tube. This procedure was repeated using chloroform isoamyl alcohol. The aqueous layer was brought to 0.3 molar sodium acetate. Nucleic acids were precipitated by adding 95% cold ethanol and storing at −70° C. for 1 hour. The concentration of HIV-I DNA was then determined at $A_{260}$ and serial dilutions of varying copy number were made in TE buffer [tris(hydroxymethyl)aminomethane (1 mmolar) and (ethylenedinitrilo)tetraacetic acid (0.1 mmolar)] for experimental use.

The high copy β-globin DNA was obtained in human placental DNA (0.5 mg/ml) which is assumed to have two copies of the β-globin gene per cell.

The leuco dye dispersion contained agarose (0.5%), 4,5-bis(4-dimethylaminophenyl)-2-(4-hydroxy- 3-methoxyphenyl)imidazole leuco dye (250 μmolar), diethylenetriaminepentaacetic acid (100 μmolar), 4'-hydroxyacetanilide (5 mmolar), polyvinylpyrrolidone (112 mmolar) and sodium phosphate, monobasic, 1-hydrate (10 mmolar).

The conjugate solution used in the Examples contained a conjugate (126 μ/l) of streptavidin and horseradish peroxidase obtained from commercial sources (Zymed Laboratories, Inc.), casein (0.5%) and merthiolate (0.5%) in phosphate buffered saline solution (24 mmolar sodium phosphate and 75 mmolar sodium chloride). The final conjugate concentration was 312 ng/ml.

The wash solution used in the Examples contained sodium chloride (373 mmolar), (ethylenedinitrilo)tetraacetic acid disodium salt (2.5 mmolar), decyl sodium sulfate (38 mmolar) and ethylmercurithiosalicylic acid, sodium salt (25 μmolar) in sodium phosphate, monobasic 1-hydrate buffer (25 mmolar, pH 7.4).

The "TP4" monoclonal antibody was used in the reaction mixture. This antibody is specific to DNA polymerase from *Thermus aquaticus* and is described in more detail in recently allowed U.S. Ser. No. 07/958,144 (noted above).

The polymerase chain reaction mixture (100 ml) contained tris(hydroxymethyl)aminomethane buffer (10 mmolar, pH 8), potassium chloride (50 mmolar), magnesium chloride (10 mmolar), dATP, dCTP, dGTP and dTTP (1.5 molar of each), primers (either 0.4 or 1 μmolar of each), gelatin (0.01%), the noted DNA polymerase (either 4 or 16 units/100 μl) and the "TP4" monoclonal antibody (50:1 molar ratio to DNA polymerase).

The remainder of the reagents and materials were obtained using commercial sources or prepared at Eastman Kodak Company using conventional procedures.

Examples 1 & 2 Detection of Amplified HIV-I DNA

These examples demonstrate the present invention to coamplify and detect a low copy target nucleic acid, HIV-I DNA, in the presence of a high copy target nucleic acid, β-globin DNA.

The PCR reaction mixture described above contained either 5 or 10 copies of HIV-I DNA, about 1 million copies of β-globin DNA, and various amounts of DNA polymerase and primers (0.4 or 1 μmolar for each primer of each primer set).

A Control PCR protocol included 40 amplification cycles, each cycle of:

1) heating at 95° C. for 15 seconds for denaturation (195 seconds on first cycle only), and 2) priming (annealing) and extension at 64° C. for 30 seconds.

The PCR protocol of this invention included:

I) 25 primary amplification cycles, each cycle of:
   A) heating at 95° C. for 15 seconds for denaturation (195 seconds on first cycle only), and
   B,C) priming (annealing) and extension at 64° C. for 30 seconds, and II) 15 secondary amplification cycles, each cycle of:
   A) heating at 95° C. for 15 seconds for denaturation, A') renaturation at 75° C. for 15 seconds (Example 1) or 30 seconds (Example 2), and B,C) priming (annealing) and extension at 64° C. for 30 seconds.

The first set of assays were carried out using 16 units of DNA polymerase/100 μl and 10 copies of HIV-I DNA in the reaction mixture. The second set of assays were carried out using 4 units of DNA polymerase/100 μl and 5 copies of HIV-I DNA in the reaction mixture.

Detection of the amplification products was accomplished in the following manner. A portion (5 μl) of the final amplification reaction mixture was mixed with a buffer solution [tris(hydroxymethyl)aminomethane (10 mmolar, pH 8), potassium chloride (50 mmolar), magnesium chloride (10 mmolar) and gelatin (0.01%)] (95 μl) and incubated at 95° C. for 5 minutes to denature the nucleic acids. The resulting solution was then transferred to SURECELL™ test devices so amplified target nucleic acids could be hybridized to the capture probes at 50° C.

The test wells of the test devices were then washed at 55° C. with a buffer solution [sodium dihydrogen phosphate (10 mmolar), sodium chloride (150 mmolar), sodium decyl sulfate (1%) and ethylenediaminetetraacetic acid (1 mmolar)] (250 μl, pH 7.4). The streptavidin-peroxidase conjugate solution (50 μl) noted above was added to each test well and allowed to flow through the membrane at room temperature. After two minutes, the test wells were washed a second time.

The leuco dye dispersion (100 μl) noted above was added to each test well, and the devices were incubated at room temperature for two minutes. A solution (100 μl) of sodium azide (0.1%) was added to stop dye development.

The resulting dye signals observed in the assays were visually graded on a density scale of 0 to 10 (highest density). The results of the assays are shown in Tables I and II below [Table I for the first set of assays (high DNA polymerase, 10 copies of HIV-I DNA), and Table II for the second set of assays (lower DNA polymerase, 5 copies of HIV-I DNA)].

As noted above, Example 1 included a 15 second renaturation step, while Example 2 included a 30 second renaturation step. The Control assay included no renaturation step.

TABLE I

| Primer Level (μmolar) | PCR Protocol | Dye Signal |
| --- | --- | --- |
| 0.4 | Control | 6.00 |
| 1 | Control | 4.00 |
| 0.4 | Example 1 | 6.75 |
| 1 | Example 1 | 7.50 |
| 0.4 | Example 2 | 8.00 |
| 1 | Example 2 | 8.00 |

TABLE II

| Primer Level (μmolar) | PCR Protocol | Dye Signal |
| --- | --- | --- |
| 0.4 | Control | 2.50 |
| 1 | Control | 0.38 |
| 0.4 | Example 2 | 4.75 |
| 1 | Example 2 | 3.00 |

It can be seen from these results that inclusion of a product renaturation step in the later cycles of PCR increases the signal obtained from amplification of the low copy target nucleic acid. This improvement was observed for both levels of DNA polymerase and primers used in the assays.

The invention has been described in detail with particular reference to preferred embodiments thereof, but it will be understood that variations and modifications can be effected within the spirit and scope of the invention.

We claim:

1. A method for the coamplification of two or more target nucleic acids, said method comprising:

I) at least 15 primary amplification cycles of from about 20 to about 360 seconds each, each cycle comprising the sequential steps of:

A) heating a reaction mixture of two or more target nucleic acids or their primer extension products, at least one of said target nucleic acids being a low copy target nucleic acid, and at least one other of sid target nucleic acids being a high copy target nucleic acid which is suspected of being present at at least about 1000 times the concentration of said low copy nucleic acid, said heating being carried out at a first temperature, $T_1$, of from about 85° to about 100° C. for denaturation of the strands of said high and low copy target nucleic acids or their primer extension products, B) priming said denatured strands with a set of primers specific to and hybridizable with opposing strands of each target nucleic acid to be amplified, by cooling to a second temperature, $T_2$, which is defined as:

$(T_{mH}-15)°C. \leq T_2 \leq (T_{mH}+5)°C.$ wherein $T_{mH}$ is the melting temperature of the primers for the high copy target nucleic acid, C) either as a continuation of step B) or in a different step, forming primer extension products in a reaction mixture of PCR reagents, by incubation at a third temperature, $T_3$, which is defined as:

$(T_{mH}-15)°C. \leq T_3 \leq (T_{mH}+15)°C.$, provided that when priming and primer extension products formation are carried out in the same step, $T_2$ and $T_3$ are the same, and II) at least 5 secondary amplification cycles of from about 20 to about 360 seconds each, each cycle comprising repeating steps A) through C) identified sequentially, provided that between steps A) and B) of each secondary amplification cycle, the reaction mixture is cooled to and maintained at a fourth temperature, $T_4$, which is defined as:

$(T_{mH}+5)°C. \leq T_4 \leq T_{PH}$ wherein $T_{PH}$ is the melting temperature of the double strands of said high copy target nucleic acid, for from about 15 to about 120 seconds, wherein the total number of primary amplification cycles and secondary amplification cycles is 55 cycles or less.

2. The method of claim 1 wherein steps B) and C) of both primary and secondary amplification cycles are carried out in the same step at the same temperature which is from about 62° to about 68° C.

3. The method of claim 1 wherein said low copy target nucleic acid is encoded by or consists of the genome of an infectious agent.

4. The method of claim 3 wherein said low copy target nucleic acid is encoded by or consists of the genome of a viral infectious agent.

5. The method of claim 4 wherein said low copy nucleic acid is encoded by or consists of the genome of either HIV-I or HIV-II.

6. The method of claim 1 wherein one or both of the primers specific for the low copy target nucleic acid are biotinylated, and detection of said low copy target nucleic acid is carried out by capturing the resulting amplified biotinylated strand using an insolubilized oligonucleotide complementary thereto, and detecting said biotinylated strand with detectably labeled streptavidin conjugate.

7. The method of claim 6 wherein said insolubilized oligonucleotide is covalently attached to a magnetic or polymeric particle.

8. The method of claim 1 wherein $T_4$ is within the range of from about 65° to about 90° C.

9. The method of claim 1 comprising from 15 to 35 primary amplification cycles and from 5 to 15 secondary amplification cycles.

10. The method of claim 1 wherein each primary and secondary amplification cycle is carried out within from about 30 to about 120 seconds.

11. The method of claim 1 wherein said reaction mixture comprises a set of primers for said low copy target nucleic acid, a set of primers for said high copy target nucleic acid, at least four different dNTP's, a thermostable DNA polymerase, and a cofactor for said DNA polymerase.

12. The method of claim 1 wherein three or more target nucleic acids are amplified using a set of primers for each target nucleic acid.

13. The method of claim 1 wherein each melting temperature is calculated using the formula:

$$T_m = 67.5 + 0.34(\% \ G+C) - 395/N$$

wherein G and C represent the number of guanine and cytosine nucleotides, respectively, and N represents the total number of nucleotides, in the oligonucleotide.

14. The method of claim 1 wherein step A) is carried out at about 95° C., steps B) and C) are combined and carried out at a temperature of about 64° C., and $T_4$ is about 75° C.

15. The method of claim 1 wherein the initial concentration of primers for both high and low copy target nucleic acids in the reaction mixture is the same.

* * * * *